(12) United States Patent
Buddington et al.

(10) Patent No.: US 7,431,939 B1
(45) Date of Patent: Oct. 7, 2008

(54) INHIBITION OF SYSTEMIC INFECTIONS IN HUMANS AND VERTEBRATES BY DIETARY FIBERS

(75) Inventors: Randal K. Buddington, Starkville, MS (US); Jan Van Loo, Leuven (BE); Anne Frippiat, Sterrebeck (BE)

(73) Assignees: Mississippi State University, Mississippi State, MS (US); Tiense Suikerraffinaderij N.V., Tienen (BE)

( * ) Notice: Subject to any disclaimer, the term of this patent is extended or adjusted under 35 U.S.C. 154(b) by 805 days.

(21) Appl. No.: 09/671,106

(22) Filed: Sep. 28, 2000

(51) Int. Cl.
*A61K 47/00* (2006.01)
*A01N 43/04* (2006.01)

(52) U.S. Cl. .................................. 424/439; 514/54

(58) Field of Classification Search ................ 424/400, 424/439, 441, 464, 484, 489, 499, 500, 502
See application file for complete search history.

(56) References Cited

U.S. PATENT DOCUMENTS

| | | | |
|---|---|---|---|
| 5,032,579 | A | 7/1991 | Speights et al. |
| 5,051,408 | A * | 9/1991 | Cooper ..................... 424/85.1 |
| 5,260,279 | A | 11/1993 | Greenberg |
| 5,502,180 | A | 3/1996 | Kunz et al. |
| 5,792,754 | A * | 8/1998 | Green et al. .................. 514/60 |
| 5,856,313 | A * | 1/1999 | Marco et al. ................... 514/22 |
| 5,972,415 | A | 10/1999 | Brassart et al. |
| 6,001,878 | A | 12/1999 | Van Leeuwen et al. |
| 6,241,983 | B1 * | 6/2001 | Paul et al. ................... 424/93.4 |
| 6,248,375 | B1 * | 6/2001 | Gilles et al. .................... 426/72 |
| 6,500,805 | B2 * | 12/2002 | Van Loo et al. ............... 514/23 |

FOREIGN PATENT DOCUMENTS

| | | |
|---|---|---|
| EP | 0 904 784 A1 | 3/1999 |
| EP | 1 428 528 A1 | 6/2004 |
| WO | 96/13271 | 5/1996 |
| WO | WO 02/26242 A2 | 4/2002 |
| WO | WO 02/26242 A3 | 4/2002 |

OTHER PUBLICATIONS

E. J. Schiffrin et al., "Immune Modulation of Blood Leukocytes in Humans by Lactic Acid Bacteria: Criteria for Strain Selection[1-3]", Am. J. Clin. Nutr., 66:515S-20S, 1997.
R. Berg et al., "Inhibition of *Candida albicans* Translocation from the Gastrointestinal Tract of Mice by Oral Administration of *Saccharomyces boulardii*", The Journal of Infectious Diseases, 168:1314-8, 1993.
Yano, et al., "Polysaccharide-Induced Protection of Carp Cyprinus-Carpio L. Against Bacterial Infection", Journal of Fish Diseases, vol. 14, No. 5, 577-582, Database Accession No. PREV199293115402 XP002194171, Biosciences Information Service, Philadelphia, PA , Abstract (1991).
Roberfroid, et al., "The Bifidogenic Nature of Chicory Inulin and Its Hydrolysis Products", Journal of Nutrition, 128, 1, 11-19, XP002194167 ISSN: 022-3166, Abstract (1998).
Gibson, "Dietary Modulation of the Human Gut Microflora Using the Prebiotics Oligofructose and Inulin", Journal of Nutrition, 129, 7 Suppl., 1438S-1441S, XP002194168 ISSN: 0022-3166, Abstract (1999).
Gianotti, et al., "Fiber-Enriched Diet Prevents Bacterial Translocation from the Intestine to Systemic Organs", Revista Italiana di Nutrizone Parenterale ed Enterale, 11, 1, 16-22, Abstract (1993).
Jenkins, et al., "Inulin, Oligofructose and Intestinal Function", Journal of Nutrition, 129, 7 Suppl., 1431S-1433S XP002194169, ISSN: 0022-3166, Abstract (1999).
Menne, et al., "Fn-type Chicory Inulin Hydrolysate has a Prebiotic Effect in Humans", Journal of Nutrition, 130, 5, 1197-1199, XP002194170, ISSN: 0022-3166, Abstract (2000).
Quan, et al., "Dietary *Bifidobacterium lactis* (HN019) Enhances Resistance to Orgal *Salmonella typhimurium* Infection in Mice", Microbiology and Immunology, 213-222, 44, 4, Database Accession No. PREV200000229776 XP002194172, Abstract (2000).
Dazhong, et al., "Elemental Diet-Induced Bacterial Translocation Associated with Systemic and Intestinal Immune Suppression", Journal of Parenteral and Enteral Nutrition, 22, 1, 37-41, Database Accession No. PREV199800097418, Abstract (1998).
Roberfroid, et al., "Dietary Fructans", Annual Review of Nutrition, 18, 117-143, XP000856009, ISBN: 0-8243-2818-3, Abstract (1998).
Roberfroid, M., "Dietary Fiber, Inulin, and Oligofructose: a Review Comparing their Physiological Effects," Critical Reviews in Food Science and Nutrition, vol. 33, No. 2, pp. 103-148, 1993.
Campbell, J.M., et al., "Selected Indigestible Oligosaccharides Affect Large Bowel Mass, Cecal and Fecal Short-Chain Fatty Acids, pH and Microflora in Rats," American Society for Nutritional Sciences, pp. 130-136, 1997.
Mao, Y., et al., "Pectin-Supplemented Enteral Diet Reduces the Severity of Methotrexate-Induced Enterocolitis in Rats," Pectin in Enterocolitis, vol. 31, No. 6, pp. 558-567, 1996.
Roberfroid, M.B., "Concepts in Functional Foods: The Case of inulin and Oligofructose," American Society for Nutritional Sciences, pp. 1398S-1401S, 1999.

(Continued)

*Primary Examiner*—Michael G. Hartley
*Assistant Examiner*—Eric E. Silverman
(74) *Attorney, Agent, or Firm*—DLA Piper US LLP

(57) ABSTRACT

The use of a dietary fiber or a mixture of dietary fibers for the manufacture of a composition, being a pharmaceutical composition or a functional food or a functional feed, for the prevention, the inhibition and/or the treatment of systemic infections in humans and in vertebrates caused by pathogenic bacteria is disclosed.

A method for the prevention, the inhibition and/or the treatment of systemic infections in humans and in vertebrates caused by pathogenic bacteria, comprising administration to said beings, orally, through tube feeding or rectally, a composition containing an effective amount of a dietary fiber or mixture of dietary fibers is also disclosed.

The dietary fiber is preferably a fructan, typically inulin and/or oligofructose, most preferably chicory inulin with an average degree of polymerization (DP) of at least 20.

21 Claims, 2 Drawing Sheets

OTHER PUBLICATIONS

Ferguson, M.J., et al., "Production of short-chain fatty acids following in vitro fermentation of saccharides, saccharide esters, fructo-oligosaccharides, starches, modified starches, modified starches and non-starch polysaccharides," Journal of the Sciences of Food and Agriculture, vol. 80, pp. 166-170, 2000.

Gibson, G.R., et al., "Dietary Modulation of the Human Colonic Microbiota: Introducing the Concept of Prebiotics," The Journal of Nutrition, vol. 125, pp. 1401-1412, 1995.

* cited by examiner

INHIBITION OF SYSTEMIC INFECTIONS IN HUMANS AND VERTEBRATES BY DIETARY FIBERS

BACKGROUND OF THE INVENTION

1. Field of the Invention

The present invention relates to the use of a dietary fiber, particularly a fructan, for the manufacture of a composition for preventing and/or inhibiting the systemic growth of pathogenic bacteria in humans and vertebrates. The present invention also relates to a method for inhibiting the systemic growth of pathogenic bacteria in humans and vertebrates by administration of a composition containing a dietary fiber, particularly a fructan.

2. Background and Prior Art

Dietary fiber is a general term that is used to describe food ingredients that are resistant to hydrolysis by the digestive secretions of humans and vertebrates (referred to in short herein by the term resistant). Historically, dietary fibers have been considered to primarily consist of lignin, cellulose, hemicellulose or pectin. However, recent interest has focused on other dietary fibers such as, e.g., resistant starch and resistant fructans, including levan, inulin and oligosaccharides.

The sources of dietary fiber vary widely and may include trees (cellulose), beet pulp from sugar beets, and extracts from plants, plant parts and fruits (e.g., gum arabic, fructans including levan from Phleum pratense, and inulin and fructo-oligosaccharide, also named oligofructose, from roots of chicory and from tubers of Dahlia and Jerusalem artichoke; citrus pectin from fruits; carrageenan from seaweed; and husks from nuts (e.g., peanut hulls). Although resistant oligosaccharides have traditionally not been considered as dietary fibers, they do meet the necessary criteria, and are now generally accepted as such. Resistant oligosaccharides and polysaccharides can also originate from bacterial activity (e.g., fructo-oligosaccharide, levan and inulin) and can also be obtained by enzymatic synthesis, e.g., fructo-oligosaccharide from sucrose. Resistant oligosaccharides can be obtained too by partial hydrolysis of resistant polysaccharides, for example fructo-oligosaccharide by partial, acidic or enzymatic hydrolysis of fructans. The terms fructo-oligosaccharide and oligofructose are used herein interchangeably.

Fructans, i.e., levan, inulin and oligofructose, commonly occur as a polydisperse mixture of chains of carbohydrates which consist mostly of fructose units and in which fructosyl-fructose linkages constitute the majority of the linkages. Fructo-oligosaccharide or oligofructose, which is in fact a fructan composed of molecules with less than 10 saccharide units, can be obtained by extraction from plant material, by partial hydrolysis, either acidic hydrolysis or enzymatic hydrolysis, of fructans, particularly inulin, as well as by enzymatic synthesis from sucrose. All these types of fructans are embraced herein by the term fructan.

Fructans, including levan, inulin and oligofructose, are well known in the art and are considered as dietary fibers. Levan consists of chains of fructose units which are mostly or exclusively connected to each other by β(2-6) linkages. A terminal glucose unit may be present or not. Inulin consists of chains of fructose units which are mostly or exclusively connected to each other by β(2-1) linkages. Most of the inulin chains terminate in one glucose unit but the presence of said glucose unit is not necessary. Levan mostly occurs as branched fructose chains, whereas inulin is composed of linear chains of fructose units but it may also occur as chains of fructose units which are branched to a larger or lesser extent.

All said fructans, i.e., levan, inulin and oligofructose, are suitable in the present invention.

Inulin occurs at concentrations of about 10 to 20% on fresh weight in chicory, dahlia tubers and Jerusalem artichoke, from which it can be isolated at industrial scale, purified, and optionally refined to remove impurities and undesired fractions of carbohydrates, according to known techniques.

Inulin can be represented by the general formulae $GF_n$ and $F_m$, wherein G represents a glucose unit, F represents a fructose unit, n represents the number of fructose units linked to the terminal glucose unit, and m represents the number of fructose units linked to each other in the carbohydrate chain. The number of saccharide units (fructose and glucose units) in one fructan molecule, i.e., the values n+1 and m in the above formulae, are commonly referred to as the degree of polymerisation, represented as (DP). A further feature of inulin is the (number) average degree of polymerisation, represented by $\overline{(DP)}$, which is the mean number of saccharide units per polysaccharide (inulin) molecule.

Inulin from chicory is commercially available as RAFTILINE® from ORAFTI, (Tienen, Belgium), in various grades such as, for example, ST (which has a $\overline{(DP)}$ of about 10 and contains in total about 8% by weight glucose, fructose and sucrose), LS (which has a $\overline{(DP)}$ of about 10 but which contains in total less than 1% by weight glucose, fructose and sucrose), and HP (which has a $\overline{(DP)}$ of $\leqq 23$, commonly of about 25, and contains in total less than 1% by weight of glucose, fructose and sucrose).

Fructo-oligosaccharide (oligofructose) consists of chains of less than 10 fructose units which are mostly or exclusively connected to each other by β(2-6) linkages or β(2-1) linkages, and a terminal glucose unit may be present.

Oligofructose is commercially available, for example as RAFTILOSE® from ORAFTI, (Tienen, Belgium), in various grades such as, for example, RAFTILOSE® P95 which contains about 95% by weight oligofructose, composed of chains with a degree of polymerisation ranging from 2 to about 7, typically with a $\overline{(DP)}$ of 3.5 to 4.5, and containing about 5% by weight in total of glucose, fructose and sucrose.

Dietary fibers can be classified based on their solubility in water and can also be classified on whether or not the dietary fiber can be used as an energy source by bacteria of the gastro-intestinal tract whereby the dietary fiber is metabolised (fermented). Fibers that can be used by gastro-intestinal bacteria are considered to be fermentable. The terms fermentable fibers and dietary fibers are used interchangeably herein.

Dietary fibers appear to have relevance in improving human and animal health. The gastro-intestinal tract of humans and vertebrates contains many species of bacteria, some of which that are commonly present are considered as beneficial, whereas others, which typically are present in the gastro-intestinal tract in case of a bacterial infection, are considered as pathogens. The term pathogenic bacteria includes herein typically pathogenic bacteria as well as putrefactive bacteria.

Beneficial bacteria include the abilities of the production of lactic acid, other short chain fatty acids, metabolites and other chemical compounds, that are known to have beneficial effects on certain bodily functions and that suppress the growth of pathogenic bacteria species in the gastro-intestinal tract, a process called inhibition. Promotion of the growth of said beneficial bacteria, such as bifidobacteria and lactobacilli, by intake of dietary fibers, particularly inulin and resistant oligosaccharides such as, e.g., oligofructose, thus results in various beneficial effects for the host, including increase of stool weight and stool frequency with reduction of constipation, reducing effects of glycemic response, effects on blood cholesterol and on HDL/LDL ratio, and effects on serum lipids. Further effects include immuno-modulating effects resulting i.a. in protective, inhibitive and/or curative effects on cancer, particularly on breast and on colon cancer. Beneficial bacteria of the gastro-intestinal tract typically include bacteria of the genus *Bifidobacterium* (Bifidus) and *Lactobacillus*.

Pathogenic bacteria may cause to the host various diseases and dysfunctions, including diarrhoea and infectious disease, such as entero-colitis, gastro-intestinal ulcers and Crohn's disease.

It is known that beneficial bacteria, particularly those of the genus *Bifidobacterium* and *Lactobacillus*, have the capacity to ferment dietary fibers, typically fructans and resistant oligosaccharides, more effectively than pathogenic intestinal bacteria. Thus, the intake of dietary fibers, particularly of fructans and/or resistant oligosaccharides, increases the density of lactic acid producing bacteria in the gastro-intestinal tract and reduces the number of undesirable Enterobacteriaceae. The latter include most pathogens such as, e.g., bacteria of the genus *Clostridia, Bacteroides, Listeria, Candida* and *Salmonella*. Accordingly, intake of dietary fibers such as fructans and/or oligofructose can be used to selectively stimulate the growth of beneficial bacteria in the gastro-intestinal tract. The improvement of the ratio beneficial/pathogenic bacteria in turn results in beneficial health effects for the host.

To prevent, control and/or remedy disorders and diseases of the gastro-intestinal tract of humans and vertebrates caused directly or indirectly by pathogenic bacteria, several approaches are used today. A first approach is the intake of antibiotics which can selectively remove a target genus of bacteria. A second approach is the intake of probiotics, which are viable, beneficial bacteria, such as bifidobacteria and lactobacilli, enabling to alter the composition and, accordingly, the metabolism of the gastro-intestinal flora, and thus to beneficially affect the host's health. A third approach involves the intake of prebiotics, i.e., dietary fibers, which increases the ratio of beneficial/pathogenic bacteria in the gastro-intestinal tract with a concurrent reduction of undesired, pathogenic and putrefactive bacteria, resulting in beneficial health effects for the host, such as, e.g., permitting faster recovery of mucosal mass and digestive capacities, and the inhibition and/or relief of gastrointestinal dysfunctions and diseases. In a fourth approach, lectins, certain monosaccharides such as, e.g., mannose, and certain organic acids such as mono-, di- and tricarboxylic acids, have also been used to selectively decrease the density of some pathogenic bacteria.

Gastro-intestinal dysfunctions and diseases, such as severe diarrhoea and gastro-enteritis often lead to disruption of the mucosal barrier which increases the risk of translocation of bacteria from the gastro-intestinal tract to the mesenteric lymph nodes and to the blood stream, often causing subsequent sepsis in the host.

Nowadays, said subsequent sepsis is commonly inhibited and treated by means of antibiotics which are administered to the infected host. Besides, in order to control the growth of pathogenic bacteria and infection of the gastro-intestinal tract, as well as to prevent subsequent systemic infection by said pathogenic bacteria in vertebrates, often antibiotics are added to feed.

However, there is a growing concern about the use of antibiotics because of the development of bacterial strains that are resistant to antibiotics and the potential impact they have on the environment. Another detriment of the treatment with some antibiotics is the disruption of the normal gastro-intestinal bacterial flora.

Accordingly, there is an ongoing search for compounds and methods for the prevention, inhibition and treatment of systemic bacterial infections which are free of one or more disadvantages presented by the compounds and methods which are currently used in this respect.

SUMMARY OF THE INVENTION

During studies of the effects of the intake of fermentable fibers on humans and vertebrates, the inventors have found that the oral administration (including administration via tube feeding) and/or the rectal administration of dietary fibers, in particular inulin and oligofructose, does not only effect the gastro-intestinal flora by stimulating the growth of beneficial bacteria and by improving the ratio of beneficial/pathogenic bacteria, but, surprisingly, also has beneficial effects on the host's response to systemic infections by pathogenic bacteria. Said findings lead to the present invention, which in one aspect, relates to the use of a dietary fiber or a mixture of dietary fibers for the manufacture of a composition, being a pharmaceutical composition or a functional food composition or a functional feed composition, for the prevention, the inhibition and/or the treatment of systemic infections in humans and in vertebrates caused by pathogenic bacteria.

In a second aspect, the present invention provides a method for the prevention, the inhibition and/or the treatment of systemic infections in humans and in vertebrates caused by pathogenic bacteria, comprising administration to a human or a vertebrate, orally, through tube feeding or rectally, of a composition, being a functional food composition, a functional feed composition or a pharmaceutical composition, containing an effective amount of a dietary fiber or a mixture of dietary fibers.

DETAILED DESCRIPTION OF THE INVENTION

Figure 1:
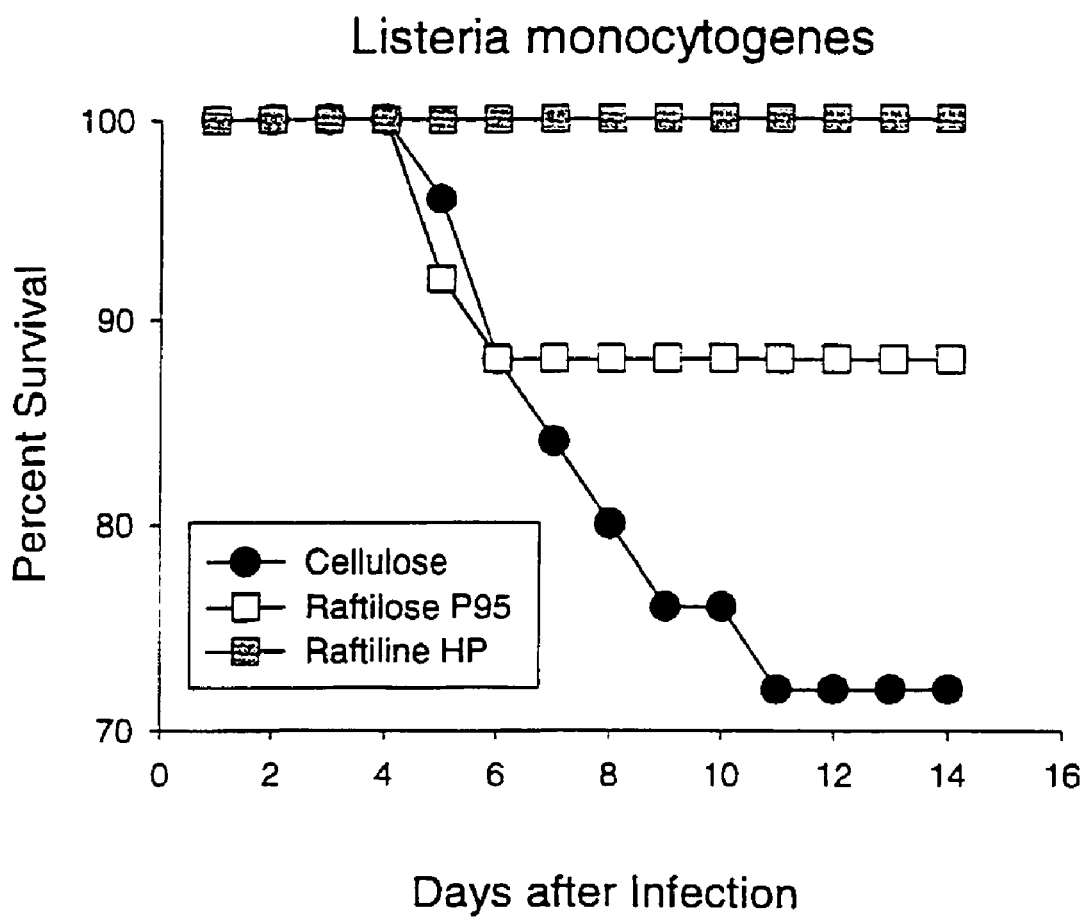
FIG. 1 shows data from a mouse model. Survival over a 14 day period is shown for mice systemically infected with *Listeria monocytogenes* which were fed a diet including (a) cellulose, (b) oligofructose and (c) inulin.

In accordance with the present invention, the term dietary fiber, also named herein interchangeably fermentable fiber, indicates an edible compound, including lignin, an oligomeric carbohydrate and a polymeric carbohydrate, that is resistant to hydrolysis by the enzymes of the digestive tract of humans and vertebrates. The term dietary fiber includes lignin, cellulose, hemicellulose, pectin, gums such as, e.g., arabic gum, carrageenan, waxes, and resistant oligosaccharides, such as, e.g., oligofructose (term interchangeably used with fructo-oligosaccharide), and resistant polysaccharides, such as, e.g., resistant starch and fructans, including levan and inulin. Preferred dietary fibers include inulin, oligofructose and mixtures thereof. More preferred fibers include chicory inulin with a $\overline{(DP)}$ of at least 20; most preferred are chicory inulin with a $\overline{(DP)}$ of at least 25.

According to the present invention, systemic infection caused by pathogenic bacteria in humans and vertebrates can be prevented, inhibited and/or treated by the oral intake and/or rectal intake of dietary fibers.

The term oral administration/oral intake herein commonly includes administration through tube feeding. Said fibers can be present in a pharmaceutical composition (medicament) together with pharmaceutically acceptable excipients, optionally in the presence of one or more additionally, physiologically active substances. Said medicament commonly occurs in a conventional galenic form that ensures it is suitable for oral administration, for tube feeding or for rectal administration, such as, e.g., tablets, lozenges, capsules, syrups, suspensions, emulsions, solutions and suppositories.

Said fibers can also be present as the functional ingredient in a functional food composition or a functional feed composition, which is a food or feed product that may provide a health benefit beyond the traditional nutrients it contains.

Preferably an effective amount of the dietary fibers, in the form of a suitable composition, is administered daily, either in a single dose form or two or more daily doses. The total daily amount of dietary fibers may widely vary and depend, e.g., on the nature of the fiber or fiber mixture, the host, and the effect aimed at, e.g., a preventive, an inhibitory or a treatment effect. The optimal daily dose commonly corresponds to the maximal amount that the host can consume without suffering from significant undesirable side effects that commonly occur with the intake of too large an amount of dietary fibers, such as flatulence and diarrhoea. The optimal dose can be found in the prior art literature and/or can be determined by the skilled person through routine experiments. For human adults the daily dose of inulin and/or oligofructose generally ranges from 5 to 40 g/day, typically the optimal dose may range from 5 to 25 g/day.

When, in accordance with the present invention, a dietary fiber or mixture of two or more dietary fibers, particularly inulin and/or oligofructose, are administered to a human or a vertebrate, a significant preventive or inhibitory effect on the systemic growth of pathogenic bacteria has been observed.

Furthermore, dietary fibers are free of toxic effects on the host and do not generate resistant bacterial strains. Furthermore, the fibers are fermented by beneficial gastro-intestinal bacteria of the host with exertion of various beneficial effects as mentioned above, and thus they have no detrimental environmental effects. Besides, the dietary fibers are obtained in an economical manner from renewable resources. Accordingly, the use of dietary fibers in accordance with the present invention for the prevention and inhibition of systemic infections in humans and vertebrates, presents considerable advantages over prior art compounds such as antibiotics.

The invention is illustrated by the examples given below.

EXAMPLE 1

Example 1 relates to a systemic infection caused by *Listeria monocytogenes*, a typical pathogenic bacteria species of the *Listeria* family which may cause a disorder named listeriosis. In most serious cases, the manifestations of listeriosis include septicemia, meningitis (or meningoencephalitis), encephalitis and intrauterine or cervical infections in pregnant woman, which may result in spontaneous abortion or stillbirth. The onset of said disorders is usually preceded by influenza-like symptoms, including headache and persistent fever. Furthermore, gastro-intestinal disorder symptoms such as nausea, vomiting and diarrhoea may precede serious forms of listeriosis or may be the only symptoms expressed.

Listeriosis is clinically defined when the organism, *Listeria monocytogenes*, is isolated from blood, cerebrospinal fluid, or an otherwise normally sterile site such as, e.g., the placenta. Listeria monocytogenes may invade the gastro-intestinal epithelium. Once the bacterium enters the host's monocytes, macrophages or polymorphonuclear leucocytes, it is bloodborne (septicemic) and can grow. Its presence intracellularly in phagocytic cells also permits access to the brain and probably transplacental migration to the fetus in pregnant women. Nearly one out of four people seriously infected by *Listeria monocytogenes* may die.

The pathogenesis of *Listeria monocytogenes* is based on its ability to survive and multiply in phagocytic host cells.

Culture of *Listeria monocytogenes*

Listeria monocytogenes of the virulent EGD strain (Erdenlig, Ainsworth, and Austin, J., Food Protection, 63:613-619, 2000) were grown on blood agar plates at 37° C. for 24 hours. The bacteria were harvested, suspended in 0.9% saline, and washed twice by centrifugation (3,2000×g; 5 min). The sedimented bacteria were again suspended in 0.9% sterile saline. The washed bacteria were propagated overnight in 37° C. tryptose broth that was shaken. The suspensions of growing bacteria were diluted to an optical density that corresponded with the desired concentration of 1 to $5\times10^7$ bacteria per ml. This was confirmed by plating aliquots on blood agar plates and enumerating the resulting colonies.

Infection of B6F3FI Mice with *Listeria monocytogenes*

The propagated *Listeria monocytogenes* was given to 25 mice by injecting with 0.1 ml intraperitoneally (infective dose of $1-5\times10^6$). The infective dose of bacteria was determined in preliminary studies that showed this dose of *Listeria monocytogenes* would result in 30-40% mortality over a 14 day period.

Preparation of Dietary Supplement Formulation

All diets were prepared as pellets by Research Diets, Inc. (New Brunswick, N.J.). The mice were fed diets based on the AIN 76 rodent diet, with 10% of the final weight as fiber (see Table 1, below). The control diet contained 10% of the insoluble and poorly fermented fiber cellulose (crystalline form). The experimental diets had the cellulose replaced entirely by oligofructose (Raftilose® P95; ORAFTI, Belgium) or inulin (Raftiline® HP; ORAFTI, Belgium), which are fermented by the gastrointestinal bacteria and differ from one another with respect to the average degree of polymerization ($\overline{DP}$) which is 4 and 25, respectively). The control and experimental diets were fed to the mice for 6 weeks before infection as presented in Table 1 below.

TABLE 1

Composition of the control and experimental diets[1] fed to the mice for 6 weeks before infection with *Listeria monocytogenes* (example 1) or *Salmonella typhimurium* (example 2). The diets continued to be fed to the mice for a 2 week period after infection.

| Ingredient | grams |
| --- | --- |
| Casein, 30 mesh | 200 |
| DL Methionine | 3 |
| Corn Starch | 150 |
| Sucrose | 450 |
| Corn Oil | 50 |
| Salt Mix S10001[2] | 35 |
| Vitamin Mix V10001[3] | 10 |

TABLE 1-continued

Composition of the control and experimental diets[1] fed to the mice for 6 weeks before infection with *Listeria monocytogenes* (example 1) or *Salmonella typhimurium* (example 2). The diets continued to be fed to the mice for a 2 week period after infection.

| Ingredient | grams |
|---|---|
| Choline Bitartrate | 2 |
| Fiber[4] | 100 |

[1] Diets were formulated and prepared by Research Diets, Inc. (New Brunswick, NJ) and were based on the AIN 76 rodent diet
[2] Composition of the salt mixture (amount in 35 g): calcium phosphate dibasic (Ca = 5.2 g; P = 4.0 g), magnesium oxide (Mg = 0.5 g), potassium citrate (K = 3.6 g), potassium sulfate (S = 0.33 g), chromium potassium sulfate (Cr = 2.0 mg), sodium choloride (Na = 1.0 g; Cl = 1.6 g), cupric carbonate (Cu = 6.0 mg), potassium iodate (I = 0.2 mg), ferric citrate (Fe = 45 mg), manganous carbonate (Mn = 59 mg), sodium selenite (Se = 0.16 mg), zinc carbonate (Zn = 29 mg), with sucrose as the remainder.
[3] Composition of the vitamin mixture (amount in 10 g): vitamin A palmitate (4,000 IU), vitamin $D_3$ (1,000 IU), vitamin E acetate (50 IU), menadione sodium bisulfate (0.5 mg menadione), biotin (0.2 mg), cyanocobalamin (10 ug), folic acid (2 mg), nicotinic acid (30 mg), calcium pantothenate (16 mg), pyridoxine-HXI (7 mg), riboflavin (6 mg), thiamin HCI (6 mg), with sucrose as the remainder.
[4] The control diet contained cellulose as the only fiber source whereas the experimental diets had either 100 g of inulin or oligofructose.

The results of example 1 are shown in FIG. 1. From the data presented in FIG. 1, it clearly follows that mice fed a diet with cellulose, a non-fermentable fiber, experienced 28% mortality when infected systemically with *Listeria monocytogenes*. In contrast, mice fed the same diet, but with oligofructose, experienced less mortality (12%) and mice fed inulin, experienced 0% mortality. These results demonstrate that a dietary supplement of oligofructose and inulin protects against systemic infections by a known pathogen.

EXAMPLE 2

Example 2 relates to a systemic infection in mice caused by *Salmonella typhimurium*.

Many species of *Salmonella* exist, several of which cause foodborne illness. *Salmonella typhimurium* has been the species that accounts for most foodborne illnesses related to *Salmonella* bacteria. Recently another species, *Salmonella enteritidis*, has been associated with foodborne diseases resulting from consumption of contaminated undercooked eggs.

Disease is caused by the penetration and passage of *Salmonella* bacteria from gut lumen into epithelium of the small intestine where inflammation occurs.

Culture of *Salmonella typhimurium*

*Salmonella typhimurium* (ATCC strain 14024) were passaged three times in B6F3F1 mice to assure virulence. Each time, *Salmonella typhimurium* were cultivated from the spleens of dead mice. The resulting virulent strain was used as the representative bacterial pathogen. The virulent *Salmonella typhimurium* were grown on blood agar plates at 37° C. for 24 hours. The bacteria were harvested, suspended in 0.9% saline, and washed twice by centrifugation (3,200×g; 5 min). The sedimented bacteria were suspended in 0.9% sterile saline to an optical density that corresponded with the desired concentration of 1 to $2\times10^4$ bacterial per ml. This was confirmed by plating aliquots on blood agar plates and enumerating the resulting colonies.

Infection of B6F3FI Mice with *Salmonella typhimurium*

The propagated *Salmonella typhimurium* were given to 25 mice by injecting with 0.1 ml intraperitoneally (infective dose of $1-5\times10^3$). The infective dose of bacteria was determined in preliminary studies that showed this dose of *Salmonella typhimurium* would result in 70-80% mortality over a 14 day period.

Preparation of Dietary Supplement Formulation

All diets were prepared as pellets by Research Diets, Inc. (New Brunswick, N.J.) and were the same as those fed to the mice in example 1 for the *L. monocytogenes* study. The mice were fed diets based on the AIN 76 rodent diet, with 10% of the final weight as fiber (see Table 1, above). The control diet contained 10% of the insoluble and poorly fermented fiber cellulose. The experimental diets had the cellulose replaced entirely by oligofructose (Raftilose® P95; ORAFTI, Belgium) or inulin (Raftiline® HP; ORAFTI, Belgium), which are fermented by the gastrointestinal bacteria and differ from one another with respect to the average degree of polymerization ($\overline{DP}$) which is 4 and 25, respectively. The control and experimental diets were fed to the mice for 6 weeks.

Figure 2:
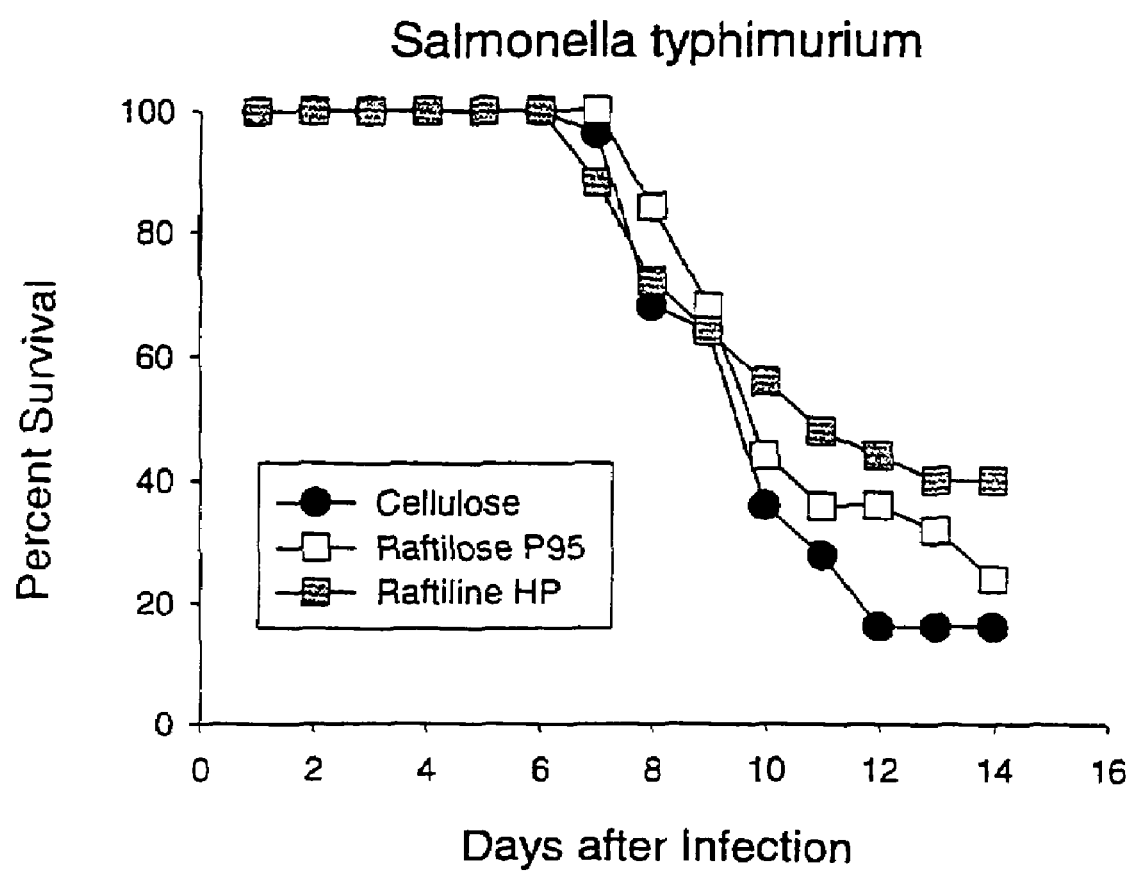
FIG. 2 shows data from a mouse model. Survival over a 14 day period is shown for mice systemically infected with *Salmonella typhimuriun* which were fed a diet including (a) cellulose, (b) oligofructose and (c) inulin.

The results of example 2 are shown in FIG. 2. From the data presented in FIG. 2, it clearly follows that mice fed a diet with cellulose, a non-fermentable fiber, experienced 82% mortality when infected systemically with *Salmonella typhimurium*. In contrast, mice fed the same diet, but with oligofructose, experienced less mortality (75%) and mice fed inulin experienced 60% mortality. The data of FIG. 2 demonstrate that mice fed diets with oligofructose and inulin experience lower mortality than control mice fed a diet with cellulose when challenged with the pathogen *Salmonella typhimurium*.

These results provide additional evidence that oligofructose and inulin provide increased resistance to systemic pathogens.

Although the present invention has been fully described by way of examples with reference to the accompanying drawings, it is to be noted that various changes and modifications will be apparent to those skilled in the art. It is therefore intended that the foregoing detailed description be understood from the following claims, including all equivalents, which are intended to define the scope of the invention. Therefore, unless such changes and modifications depart from the scope of the invention, they should be construed as being included therein.

What is claimed is:

1. A method for the treatment of infections in humans or vertebrates consisting of:
   administering to humans or vertebrates having an infection caused by an invasion of the blood stream or lymph by a pathogen selected from the group consisting of *Clostridia*, *Bacteroides*, *Listeria*, *Candida* and *Salmonella*, a composition consisting essentially of:
      an effective amount of inulin and/or oligofructose to treat said infection; and
      one or more pharmaceutically acceptable excipients,
   wherein the composition is administered orally or through tube feeding.

2. The method according to claim 1, wherein the inulin is chicory inulin with an average degree of polymerization ($\overline{DP}$) of at least 20.

3. The method according to claim 2, wherein the inulin is chicory inulin with an average degree of polymerization ($\overline{DP}$) of at least 25.

4. The method of claim 1, wherein the human or vertebrate is an adult human and the amount of inulin administered to the adult human ranges from 5 to 40 g/day.

5. The method of claim 1, wherein the human or vertebrate is an adult human and the amount of inulin administered to the adult human ranges from 5 to 25 g/day.

6. The method of claim 1, wherein the human or vertebrate is a vertebrate and wherein the inulin is chicory inulin with an average degree of polymerization ($\overline{DP}$) of at least 20.

7. The method according to claim 6, wherein the inulin is chicory inulin with an average degree of polymerization ($\overline{DP}$) of at least 25.

8. The method of claim 1, wherein said composition consists essentially of an effective amount of oligofructose.

9. A method for the treatment of an infection occupying the lymph or blood in humans or vertebrates consisting of:
   administering to humans or vertebrates having an infection caused by a pathogen selected from the group consisting of *Clostridia, Bacteroides, Listeria, Candida* and *Salmonella* in the lymph or blood, a composition consisting essentially of:
      an effective amount of inulin and/or oligofructose to treat said infection; and
      one or more pharmaceutically acceptable excipients,
   wherein the composition is administered orally or through tube feeding.

10. The method according to claim 9, wherein the inulin is chicory inulin with an average degree of polymerization ($\overline{DP}$) of at least 20.

11. The method according to claim 9, wherein the inulin is chicory inulin with an average degree of polymerization ($\overline{DP}$) of at least 25.

12. The method of claim 9, wherein the human or vertebrate is an adult human and the amount of inulin administered to the adult human ranges from 5 to 40 g/day.

13. The method of claim 9, wherein the human or vertebrate is an adult human and the amount of inulin administered to the adult human ranges from 5 to 25 g/day.

14. The method of claim 9, wherein the human or vertebrate is a vertebrate and wherein the inulin is chicory inulin with an average degree of polymerization ($\overline{DP}$) of at least 20.

15. The method according to claim 14, wherein the inulin is chicory inulin with an average degree of polymerization ($\overline{DP}$) of at least 25.

16. The method of claim 9, wherein said composition consists essentially of an effective amount of oligofructose.

17. A method for the treatment of infections in humans or vertebrates, consisting of:
   administering to humans of vertebrates having an infection caused by an invasion of the blood stream or lymph by a pathogen selected from the group consisting of *Clostridia, Bacteroides, Listeria, Candida* and *Salmonella*, a functional food composition consisting of traditional nutrients and an effective amount of inulin and/or oligofructose to treat said infection;
   wherein the food composition is administered orally or through tube feeding.

18. The method of claim 17, wherein the human or vertebrate is a vertebrate and wherein the inulin is chicory inulin with an average degree of polymerization ($\overline{DP}$) of at least 20.

19. The method according to claim 17, wherein the inulin is chicory inulin with an average degree of polymerization ($\overline{DP}$) of at least 25.

20. The method of claim 17, wherein said food composition consists of traditional nutrients and an effective amount of oligofructose.

21. The method of claim 17, wherein the human or vertebrate is an adult human and the amount of inulin administered to the adult human ranges from 5 to 40 g/day.

\* \* \* \* \*